United States Patent

Michihata

(10) Patent No.: US 11,367,182 B2
(45) Date of Patent: Jun. 21, 2022

(54) MEDICAL IMAGE PROCESSING DEVICE, IMAGE PROCESSING METHOD, AND COMPUTER READABLE RECORDING MEDIUM

(71) Applicant: Sony Olympus Medical Solutions Inc., Tokyo (JP)

(72) Inventor: Taihei Michihata, Kanagawa (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 212 days.

(21) Appl. No.: 16/729,518

(22) Filed: Dec. 30, 2019

(65) Prior Publication Data

US 2020/0273163 A1 Aug. 27, 2020

(30) Foreign Application Priority Data

Feb. 25, 2019 (JP) .............................. JP2019-032069

(51) Int. Cl.
  *G06T 7/00* (2017.01)
  *A61B 1/00* (2006.01)
  *G06T 3/40* (2006.01)

(52) U.S. Cl.
  CPC ........ *G06T 7/0012* (2013.01); *A61B 1/00009* (2013.01); *A61B 1/00045* (2013.01);
  (Continued)

(58) Field of Classification Search
  CPC ....... G06T 3/40; G06T 3/4092; G06T 7/0012; G06T 2207/10068; G06T 2207/20172;
  (Continued)

(56) References Cited

U.S. PATENT DOCUMENTS 7,429,242 B2 * 9/2008 Kawata .............. H04N 5/23225
 600/109
9,486,123 B2 * 11/2016 Morita ............... A61B 1/00188
(Continued)

FOREIGN PATENT DOCUMENTS

JP 07-148111 A 6/1995
JP 2015012958 A * 1/2015

*Primary Examiner* — Katrina R Fujita
(74) *Attorney, Agent, or Firm* — Xsensus, LLP

(57) ABSTRACT

A medical image processing device includes: a memory; and a processor including hardware. The processor is configured to: generate, by performing enlargement processing or shrinking processing to first observation image information input from an outside, second observation image information having number of pixels different from predetermined number of pixels, the first observation image information being generated by capturing a subject and having the predetermined number of pixels; generate third observation image information by performing enhancement processing for enhancing a structure of the subject to the second observation image information, the structure of the subject being contained in a second observation image corresponding to the second observation image information; and generate and output fourth observation image information having different number of pixels from that of the second observation image information by performing enlargement processing or shrinking processing to the third observation image information.

15 Claims, 5 Drawing Sheets

(52) U.S. Cl.
CPC ...... *G06T 3/40* (2013.01); *G06T 2207/20172* (2013.01); *G06T 2207/30004* (2013.01)

(58) Field of Classification Search
CPC . G06T 2207/20192; G06T 2207/30004; A61B 1/00009; A61B 1/00045
See application file for complete search history.

(56) References Cited

U.S. PATENT DOCUMENTS

| | | | |
|---|---|---|---|
| 2005/0231591 A1* | 10/2005 | Abe | H04N 5/335 348/65 |
| 2007/0041655 A1* | 2/2007 | Ozawa | G06T 5/20 382/266 |
| 2007/0273759 A1* | 11/2007 | Krupnick | H04N 5/225 348/45 |
| 2012/0201433 A1* | 8/2012 | Iwasaki | A61B 1/00009 382/128 |
| 2012/0262559 A1* | 10/2012 | On | A61B 1/00009 348/208.4 |
| 2016/0088267 A1* | 3/2016 | Niijima | H04N 9/735 348/237 |
| 2017/0034437 A1* | 2/2017 | Kutsuma | G06T 1/00 |
| 2017/0039454 A1* | 2/2017 | Sudo | G06F 3/147 |
| 2017/0163972 A1* | 6/2017 | Kohler | H04N 5/23216 |
| 2017/0251196 A1* | 8/2017 | Kiniwa | A61B 1/04 |
| 2018/0068413 A1* | 3/2018 | Nakazono | G06T 1/20 |
| 2018/0289443 A1* | 10/2018 | Wade | A61B 1/0005 |
| 2019/0158707 A1* | 5/2019 | Yokouchi | A61B 1/045 |
| 2019/0269298 A1* | 9/2019 | Kiba | G16H 40/63 |
| 2020/0129044 A1* | 4/2020 | Yamaoka | A61B 1/045 |

* cited by examiner

MEDICAL IMAGE PROCESSING DEVICE, IMAGE PROCESSING METHOD, AND COMPUTER READABLE RECORDING MEDIUM

This application claims priority from Japanese Application No. 2019-032069, filed on Feb. 25, 2019, the contents of which are incorporated by reference herein in its entirety.

BACKGROUND

The present disclosure relates to a medical image processing device, an image processing method, and a computer readable recording medium.

In endoscopes, known is a technique for performing enlargement processing to a digital image output from a charge coupled device (CCD), performing enhancement processing to the image, and then outputting the image to a display device (for example, refer to JP 7-148111 A).

SUMMARY

Meanwhile, in recent years, in the endoscope, to each of a plurality of display devices having different resolutions, an image that matches the resolution of the display device is generated and output. However, in JP 7-148111 A described above, only a display device having a certain resolution is assumed. Thus, in a case in which an image is output to a plurality of display devices having different resolutions, there is a problem in which an edge of the image is blurred, and in which noise is generated.

There is a need for a medical image processing device, an image processing method, and a computer readable recording medium for preventing an edge of an image from being blurred and enabling noise to be reduced even in a case in which the image is output to a plurality of display devices having different resolutions.

According to one aspect of the present disclosure, there is provided a medical image processing device including: a memory; and a processor including hardware, wherein the processor is configured to: generate, by performing enlargement processing or shrinking processing to first observation image information input from an outside, second observation image information having number of pixels different from predetermined number of pixels, the first observation image information being generated by capturing a subject and having the predetermined number of pixels; generate third observation image information by performing enhancement processing for enhancing a structure of the subject to the second observation image information, the structure of the subject being contained in a second observation image corresponding to the second observation image information; and generate and output fourth observation image information having different number of pixels from that of the second observation image information by performing enlargement processing or shrinking processing to the third observation image information.

DETAILED DESCRIPTION

Hereinbelow, modes for carrying out the present disclosure (hereinbelow referred to as "embodiments") will be described in detail with reference to the drawings. Note that the present disclosure is not limited by the following embodiments. Also, each figure referred to in the following description merely illustrates a shape, a size, and a positional relationship as schematically as the content of the present disclosure may be understood. That is, in the present disclosure, the shape, the size, and the positional relationship are not limited to those illustrated in each figure. Further, to illustrate figures, identical components are labeled with the same reference signs. Still further, as an example of a medical observation system according to the present disclosure, an endoscope system will be described.

First Embodiment

Figure 1:
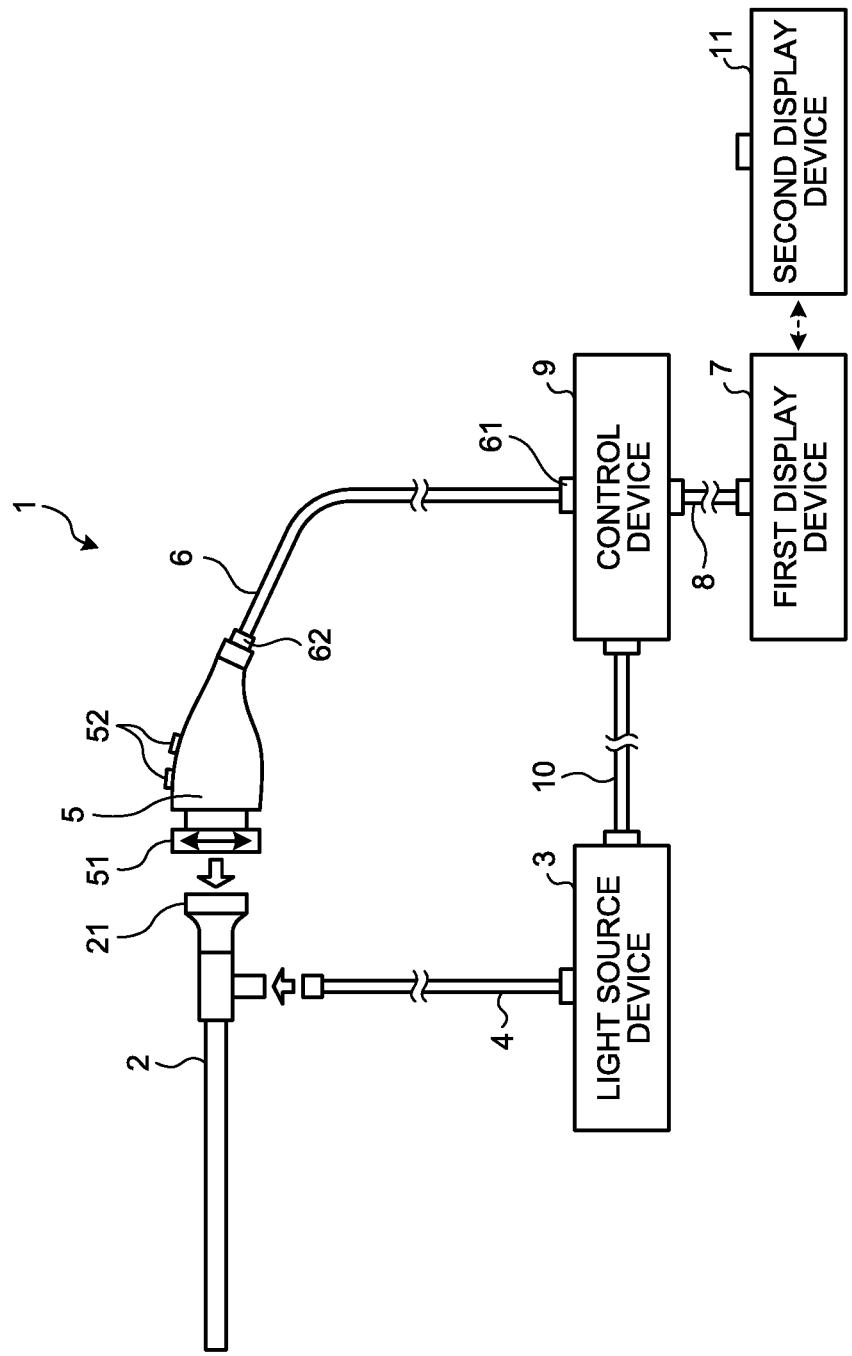
FIG. 1 illustrates a schematic configuration of an endoscope system according to a first embodiment.

FIG. 1 illustrates a schematic configuration of an endoscope system according to a first embodiment. An endoscope system 1 illustrated in FIG. 1 is a system used in a medical field, inserted into an inside of a subject such as a living body of a human being or an animal (into a living body), and displaying an image obtained by capturing an image of the inside to cause the subject to be observed. Note that, in the first embodiment, although a rigid endoscope system using a rigid endoscope (insertion unit 2) illustrated in FIG. 1 will be described as the endoscope system 1, the endoscope system 1 may be a flexible endoscope system, for example.

The endoscope system 1 illustrated in FIG. 1 includes the insertion unit 2 (endoscope), a light source device 3, a light guide 4, a camera head 5 (imaging device for the endoscope), a first transmission cable 6, a first display device 7, a second transmission cable 8, a control device 9, a third transmission cable 10, and a second display device 11.

The insertion unit 2 is rigid or at least partially flexible, is formed in an elongated shape, and is inserted into the subject such as a patient. Inside the insertion unit 2 is provided an optical system including one or a plurality of lenses and forming an observation image.

To the light source device 3, one end of the light guide 4 is connected. The light source device 3 emits (supplies) light adapted to illuminate the inside of the subject to the one end of the light guide 4 under control of the control device 9. The light source device 3 includes a light emitting diode (LED) light source or a semiconductor laser element such as a laser diode (LD) emitting white light.

The one end of the light guide 4 is removably connected to the light source device 3, and the other end is removably connected to the insertion unit 2. The light guide 4 guides light emitted from the light source device 3 from the one end to the other end and supplies the light to the insertion unit 2.

To the camera head 5, an ocular unit 21 of the insertion unit 2 is removably connected. The camera head 5 captures an observation image formed by the insertion unit 2 to generate an imaging signal, converts the imaging signal (electric signal) into an optical signal, and outputs the optical signal under control of the control device 9. Also, the camera head 5 includes an operation ring unit 51 provided to be rotatable in a circumferential direction and a plurality of input units 52 receiving input of an instruction signal instructing various operations of the endoscope system 1.

One end of the first transmission cable 6 is removably connected to the control device 9 via a first connector unit 61, and the other end is connected to the camera head 5 via a second connector unit 62. The first transmission cable 6 transmits an imaging signal output from the camera head 5 to the control device 9 and transmits a control signal, a synchronization signal, a clock signal, electric power, and the like output from the control device 9 to the camera head 5.

The first display device 7 may be connected to the control device 9 via the second transmission cable 8 and displays a display image based on an image signal processed in the control device 9 (hereinbelow referred to as "a first display image") or various kinds of information regarding the endoscope system 1 under control of the control device 9. Also, the monitor size of the first display device 7 is 31 inches or larger, and preferably 55 inches or larger. Meanwhile, in the first embodiment, although the monitor size of the first display device 7 is 31 inches or larger, the monitor size is not limited to this as long as the monitor size enables an image having the number of pixels for a Full HD image, such as an image having a resolution of two mega pixels (for example, a resolution of 1920×1080 pixels, that is, 2K pixels) or more, to be displayed.

One end of the second transmission cable 8 is removably connected to the first display device 7 or the second display device 11, and the other end is removably connected to the control device 9. The second transmission cable 8 transmits to the first display device 7 or the second display device 11 the display image based on the image signal processed in the control device 9.

The control device 9 includes a memory and a processor including hardware such as a central processing unit (CPU), a graphics processing unit (GPU), an application specific integrated circuit (ASIC), and a field programmable gate array (FPGA) and comprehensively controls operations of the light source device 3, the camera head 5, the first display device 7, and the second display device 11 via the first transmission cable 6, the second transmission cable 8, and the third transmission cable 10 in accordance with a program recorded in the memory.

One end of the third transmission cable 10 is removably connected to the light source device 3, and the other end is removably connected to the control device 9. The third transmission cable 10 transmits a control signal from the control device 9 to the light source device 3.

The second display device 11 may be connected to the control device 9 via the second transmission cable 8 and displays a display image based on an image signal processed in the control device 9 (hereinbelow referred to as "a second display image") or various kinds of information regarding the endoscope system 1 under control of the control device 9. The second display device 11 is formed with use of liquid crystal, organic EL, or the like. Also, the monitor size of the second display device 11 is 31 inches or larger, and preferably 55 inches or larger. Meanwhile, in the first embodiment, although the monitor size of the second display device 11 is 31 inches or larger, the monitor size is not limited to this as long as the monitor size enables an image having as many pixels as a 4K image, such as an image having a resolution of eight mega pixels (for example, a resolution of 3840×2160 pixels, that is, 4K pixels) or more, more preferably having a resolution of 32 mega pixels (for example, a resolution of 7680×4320 pixels, that is, 8K pixels) or more, to be displayed.

Detailed Configurations of Camera Head and Control Device

Figure 2:
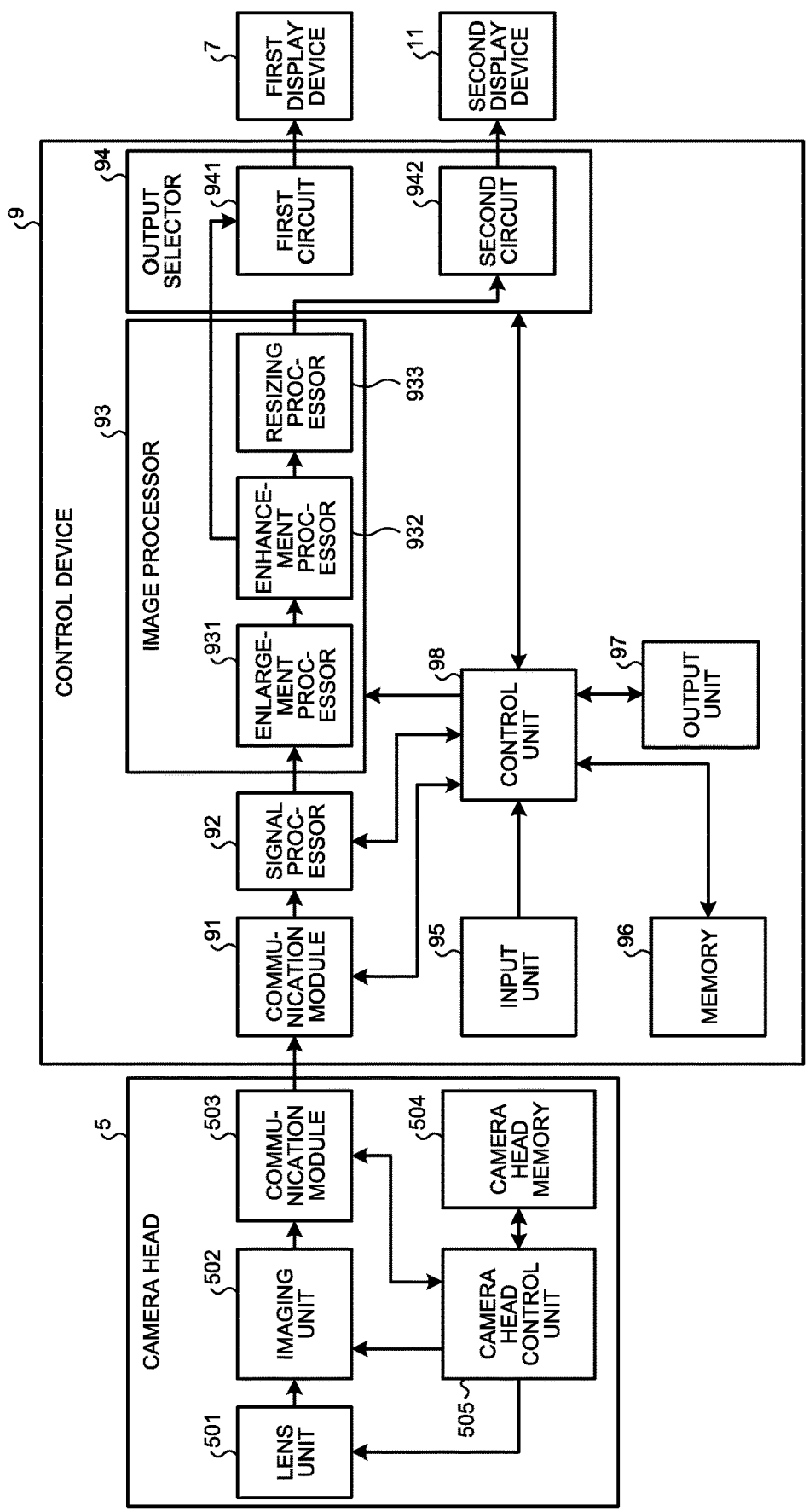
FIG. 2 is a block diagram illustrating functional configurations of a camera head and a control device included in the endoscope system according to the first embodiment.

Next, detailed configurations of the camera head 5 and the control device 9 will be described. FIG. 2 is a block diagram illustrating functional configurations of the camera head 5 and the control device 9 included in the endoscope system 1. Note that, in FIG. 2, the insertion unit 2, the light source device 3, the light guide 4, the first transmission cable 6, the second transmission cable 8, and the third transmission cable 10 are omitted for convenience of description.

Configuration of Camera Head

First, a configuration of the camera head 5 will be described.

The camera head 5 includes a lens unit 501, an imaging unit 502, a communication module 503, a camera head memory 504, and a camera head control unit 505.

The lens unit 501 is formed with use of one or a plurality of lenses and forms a subject image on a light receiving surface of the imaging unit 502. Also, the lens unit 501 performs auto focus (AF) in which a not-illustrated driver moves the lens along a light axial direction to change a focal position and optical zoom in which the driver changes a focal length under control of the camera head control unit 505. Note that, in the first embodiment, the lens unit 501 may be provided with a diaphragm mechanism and an optical filter mechanism removable on the light axis.

The imaging unit 502 (imaging device) receives a subject image formed by the insertion unit 2 and the lens unit 501, performs photoelectric conversion to generate an imaging signal (RAW data), and outputs the imaging signal to the communication module 503 under control of the camera head control unit 505. The imaging unit 502 is formed with use of a charge coupled device (CCD), a complementary metal oxide semiconductor (CMOS), or the like. The imaging unit 502 has a resolution of two mega pixels (for example, a resolution of 1920×1080 pixels, that is, 2K pixels) or less, for example.

The communication module 503 outputs various signals transmitted via the first transmission cable 6 from the control device 9 to the respective units in the camera head 5. The communication module 503 also performs parallel-serial conversion processing or the like to an imaging signal generated by the imaging unit 502, information regarding a current state of the camera head 5, or the like and outputs the signal or the like via the first transmission cable 6 to the control device 9.

The camera head memory 504 stores camera head information identifying the camera head 5 and various programs to be executed by the camera head 5. Here, the camera head information includes the number of pixels of the imaging unit 502, an identification ID of the camera head 5, and the like. The camera head memory 504 is formed with use of a volatile memory, a non-volatile memory, and the like. Here, the camera head memory 504 may be provided in the connector unit 61, instead of in the camera head 5.

The camera head control unit 505 controls operations of the respective units included in the camera head 5 based on various signals input from the communication module 503. The camera head control unit 505 is formed with use of a memory and a processor including hardware such as a CPU.

Configuration of Control Device

Next, a configuration of the control device 9 will be described.

The control device 9 includes a communication module 91, a signal processor 92, an image processor 93, an output selector 94, an input unit 95, a memory 96, an output unit 97, and a control unit 98.

The communication module 91 outputs various signals including an imaging signal input from the camera head 5 to the control unit 98 and the signal processor 92. The communication module 91 also transmits various signals input from the control unit 98 to the camera head 5. Specifically, the communication module 91 performs parallel-serial conversion processing or the like to a signal input from the control unit 98 and outputs the signal to the camera head 5. The communication module 91 also performs parallel-serial conversion processing or the like to a signal input from the camera head 5 and outputs the signal to the respective units included in the control device 9.

The signal processor 92 performs signal processing such as noise reduction processing and A/D conversion processing to an imaging signal input via the communication module 91 from the camera head 5 and outputs the signal to the image processor 93.

The image processor 93 performs various kinds of image processing to an imaging signal input from the signal processor 92 and outputs the signal to the output selector 94 under control of the control unit 98. Here, the predetermined image processing includes various kinds of known image processing such as interpolation processing, color correction processing, color enhancement processing, and edge enhancement processing. The image processor 93 is formed with use of a memory and a processor including hardware such as a GPU, an FPGA, and a CPU. Also, in the first embodiment, the image processor 93 functions as a medical image processing device. Also, the image processor 93 includes at least an enlargement processor 931, an enhancement processor 932, and a resizing processor 933.

The enlargement processor 931 executes enlargement processing to first observation image information input from the signal processor 92 under control of the control unit 98. Specifically, the enlargement processor 931 executes enlargement processing for enlarging the number of pixels to the first observation image information having the number of pixels of 2K or less so that the first observation image information may be image data having the number of pixels of 2K or more to generate second observation image information.

The enhancement processor 932 executes enhancement processing to the second observation image information input from the enlargement processor 931 to generate third observation image information and outputs the third observation image information to the output selector 94 under control of the control unit 98. Here, the enhancement processing is processing for enhancing the structure and the edge of the subject such as enhancement processing. Meanwhile, the enhancement processor 932 may perform noise reduction processing as well as the enhancement processing.

The resizing processor 933 executes enlargement processing or shrinking processing to the third observation image information input from the enhancement processor 932 under control of the control unit 98. Specifically, the resizing processor 933 executes enlargement processing for enlarging the number of pixels to the third observation image information having the number of pixels of 2K so that the third observation image information may be image data having the number of pixels of 4K to generate fourth observation image information and outputs the fourth observation image information to the output selector 94.

To the output selector 94, at least either the first display device 7 or the second display device 11 is connected. The output selector 94 includes a first circuit 941 connected to the first display device 7 and outputting the third observation image information to the first display device 7 and a second circuit 942 connected to the second display device 11 and outputting the fourth observation image information to the second display device 11.

The input unit 95 is formed with use of a keyboard, a mouse, a touch panel, and the like. The input unit 95 receives input of various kinds of information by means of a user's operation.

The memory 96 is formed with use of a volatile memory, a non-volatile memory, a frame memory, and the like. The memory 96 stores various programs executed by the endoscope system 1 and various kinds of data used during processing. Note that the memory 96 may further include a memory card attachable to the control device 9.

The output unit 97 is formed with use of a loudspeaker, a printer, a display, and the like. The output unit 97 outputs various kinds of information regarding the endoscope system 1.

The control unit 98 comprehensively controls the respective units included in the endoscope system 1. The control unit 98 is formed with use of a memory and hardware such as a CPU.

Processing of Control Device

Next, processing that the control device 9 executes will be described.

Figure 3:
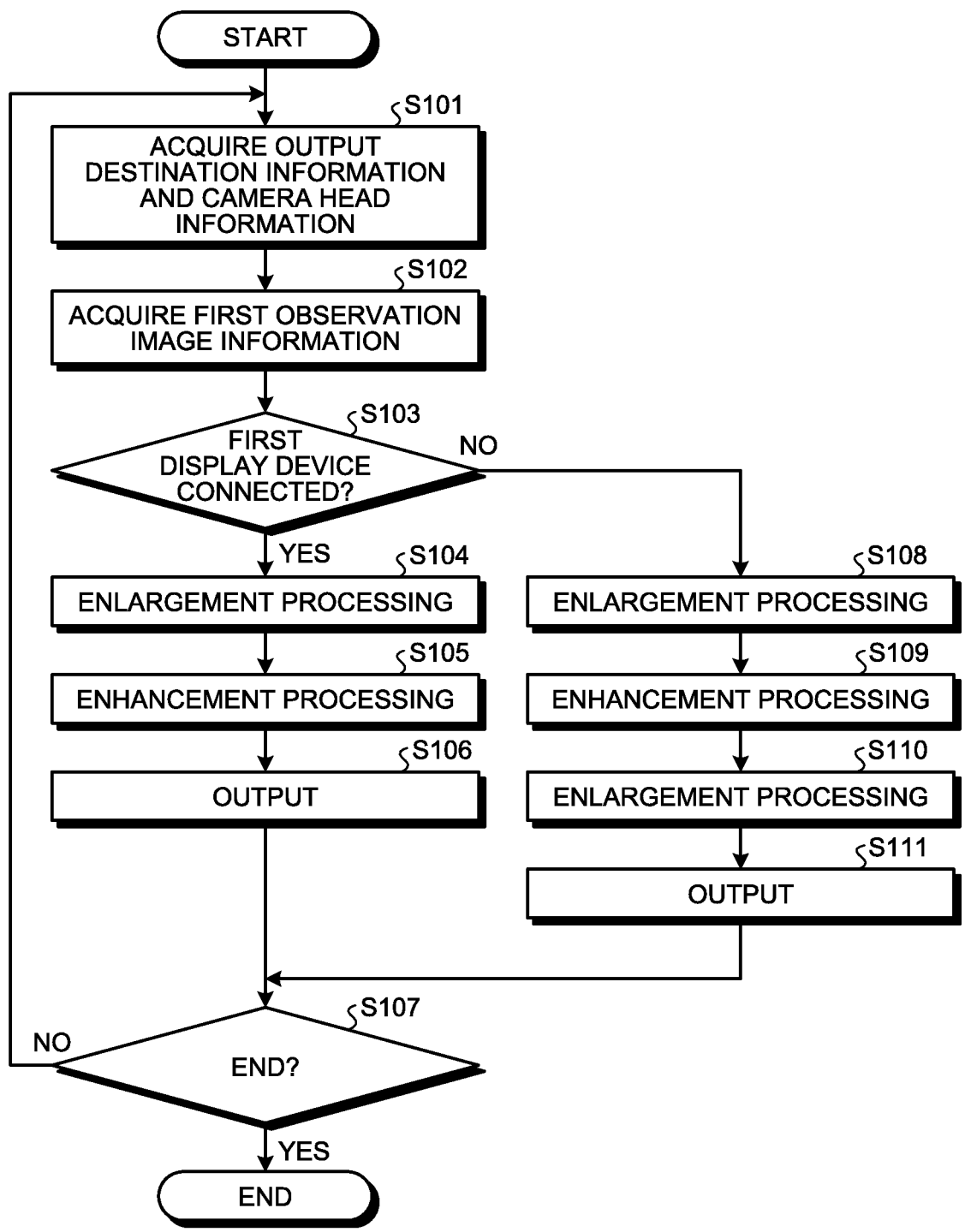
FIG. 3 is a flowchart illustrating an overview of processing that a control device 9 according to the first embodiment executes.

FIG. 3 is a flowchart illustrating an overview of processing that the control device 9 executes.

As illustrated in FIG. 3, the control unit 98 first acquires output destination information indicating a resolution of a display device to which the output selector 94 is to output information and camera head information indicating a resolution of the camera head 5 via the communication module 91 (step S101).

Subsequently, the control unit 98 acquires first observation image information, which is an imaging signal generated by the camera head 5, via the communication module 91 (step S102).

The control unit 98 thereafter determines based on the output destination information whether or not the first display device 7 is connected to the output selector 94 (step S103). In a case in which the control unit 98 determines that the first display device 7 is connected to the output selector 94 (step S103: Yes), the control device 9 moves to step S104 described below. Conversely, in a case in which the control unit 98 determines that the first display device 7 is not connected to the output selector 94 (step S103: No), the control device 9 moves to step S108 described below.

In step S104, the enlargement processor 931 executes enlargement processing to the first observation image information input from the signal processor 92 under control of the control unit 98. Specifically, the enlargement processor 931 executes enlargement processing for enlarging the number of pixels to the first observation image information having the number of pixels of 2K or less so that the first observation image information may be image data having the number of pixels of 2K or more to generate second observation image information and outputs the second observation image information to the enhancement processor 932.

Subsequently, the enhancement processor 932 executes enhancement processing for enhancing a structure of a subject contained in a second observation image corresponding to the second observation image information to the second observation image information input from the enlargement processor 931 to generate third observation image information, in which the structure of the subject is enhanced, and outputs the third observation image information to the first circuit 941 of the output selector 94 under control of the control unit 98 (step S105).

The first circuit 941 thereafter outputs the third observation image information to the first display device 7 under control of the control unit 98 (step S106). Consequently, the first display device 7 may display a first display image having 2K image quality corresponding to the third observation image information in which the structure of the subject is enhanced, and in which noise is reduced.

Subsequently, in a case in which an instruction signal for ending observation of the subject is input from the input unit 95 (step S107: Yes), the control device 9 ends the processing. Conversely, in a case in which an instruction signal for ending observation of the subject is not input from the input unit 95 (step S107: No), the control device 9 returns to step S101 described above.

In step S108, the enlargement processor 931 executes enlargement processing to the first observation image information input from the signal processor 92 under control of the control unit 98. Specifically, the enlargement processor 931 executes enlargement processing for enlarging the number of pixels to the first observation image information having the number of pixels of 2K or less so that the first observation image information may be image data having the number of pixels of 2K or more to generate second observation image information and outputs the second observation image information to the enhancement processor 932.

Subsequently, the enhancement processor 932 executes enhancement processing for enhancing a structure of a subject contained in a second observation image corresponding to the second observation image information to the second observation image information input from the enlargement processor 931 to generate third observation image information, in which the structure of the subject is enhanced, and outputs the third observation image information to the resizing processor 933 under control of the control unit 98 (step S109).

The resizing processor 933 thereafter executes enlargement processing to the third observation image information input from the enhancement processor 932 under control of the control unit 98 (step S110). Specifically, the resizing processor 933 executes enlargement processing for enlarging the number of pixels to the third observation image information having the number of pixels of 2K so that the third observation image information may be image data having the number of pixels of 4K to generate fourth observation image information and outputs the fourth observation image information to the second circuit 942 of the output selector 94.

Subsequently, the second circuit 942 outputs the fourth observation image information to the second display device 11 under control of the control unit 98 (step S111). Consequently, the second display device 11 may display a second display image having 4K image quality corresponding to the fourth observation image information in which the structure of the subject is enhanced, and in which noise is reduced. After step S111, the control device 9 moves to step S107.

According to the first embodiment described above, the image processor 93 performs enlargement processing to first observation image information input from the camera head 5 via the communication module and the signal processor 92 to generate second observation image information having the different number of pixels from that of the first observation image information, performs enhancement processing for enhancing a structure of a subject contained in a second observation image corresponding to the second observation image information to the second observation image information to generate third observation image information, and performs enlargement processing to the third observation image information to generate and output fourth observation image information having the different number of pixels from that of the second observation image information. Accordingly, even in a case in which an image is output to the first display device 7 or the second display device 11 having different resolutions, the edge of the image may be prevented from being blurred, and noise may be reduced.

Also, according to the first embodiment, the image processor 93 outputs the third observation image information to the first circuit 941 and outputs the fourth observation image information to the second circuit 942. Accordingly, even in a case in which an image is output to the first display device 7 or the second display device 11 having different resolutions, the edge of the image may be prevented from being blurred, and noise may be reduced.

Also, according to the first embodiment, the image processor 93 performs enlargement processing to the first observation image information to generate the second observation image information and performs enlargement processing to the third observation image information to generate the fourth observation image information. Accordingly, even in a case in which an image is output to the first display device 7 or the second display device 11 having different resolutions, the edge of the image may be prevented from being blurred, and noise may be reduced.

Also, according to the first embodiment, the image processor 93 performs enlargement processing to the first observation image information to generate the second observation image information having as many pixels as a Full HD image and performs enlargement processing to the third observation image information having as many pixels as the Full HD image to generate the fourth observation image information having as many pixels as a 4K image. Accordingly, even in a case in which an image is output to the first display device 7 or the second display device 11 having different resolutions, the edge of the image may be prevented from being blurred, and noise may be reduced.

Meanwhile, in the first embodiment, although the image processor 93 performs the enlargement processing, the enhancement processing, and the enlargement processing to generate the fourth observation image information and outputs the fourth observation image information to the second display device 11, the processing may appropriately be changed in accordance with the resolution of an image that may be displayed on the first display device 7 or the second display device 11. Specifically, the image processor 93 may perform enlargement processing to the first observation image information to generate the second observation image information and perform shrinking processing to the third observation image processing to generate the fourth observation image information. More specifically, the image processor 93 may perform enlargement processing to the first observation image information to generate the second observation image information having as many pixels as a 4K image and perform shrinking processing to the third observation image processing having as many pixels as the 4K image to generate the fourth observation image information having as many pixels as a Full HD image. Accordingly, even in a case in which an image is output to the first display device 7 or the second display device 11 having different resolutions, the edge of the image may be prevented from being blurred, and noise may be reduced.

Also, in the first embodiment, although the output selector 94 is provided with the first circuit 941 and the second circuit 942, the present embodiment is not limited to this. The output selector 94 may be provided with only one output circuit, and the image processor 93 may change the processing content of the image processing in accordance with the resolution of the first display device 7 or the second display device 11 connected to this output circuit.

Also, in the first embodiment, the second display device 11 has only to be able to display an image having higher resolution than that of the first display device 7. For example, in a case in which the second display device 11 has a monitor size having a resolution of 8K, the first display device 7 may have a monitor size having a resolution of 4K. At this time, the enlargement processor 931 may generate a 4K image, and the resizing processor 933 may generate an 8K image.

Second Embodiment

Next, a second embodiment will be described. Although a case in which the present disclosure is applied to the rigid endoscope system using the rigid endoscope has been described in the aforementioned first embodiment, a case in which the present disclosure is applied to a flexible endoscope system using a flexible endoscope will be described in the second embodiment. Note that similar components to those in the endoscope system 1 according to the aforementioned first embodiment are labeled with the same reference signs, and description of the duplicate components is omitted.

Schematic Configuration of Endoscope System

Figure 4:
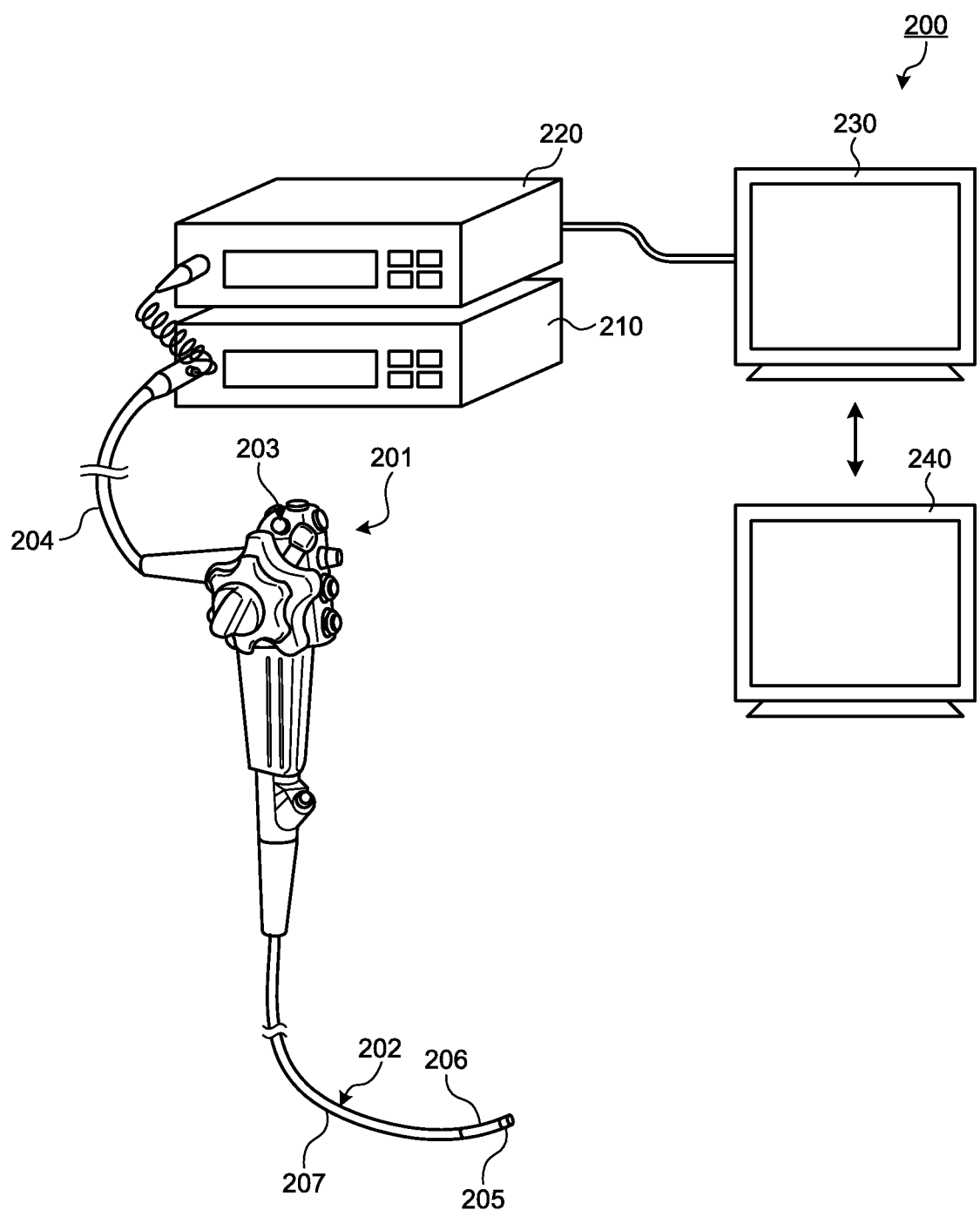
FIG. 4 illustrates a schematic configuration of an endoscope system according to a second embodiment.

FIG. 4 illustrates a schematic configuration of an endoscope system according to a second embodiment. An endoscope system 200 illustrated in FIG. 4 includes an endoscope 201 having an insertion unit 202 thereof inserted into a subject to capture an in-vivo image of an observed region and generate an imaging signal, a light source device 210 supplying illumination light to the endoscope 201, a control device 220 performing predetermined image processing to the imaging signal that the endoscope 201 has acquired and comprehensively controlling operations of the entire endoscope system 200, a first display device 230 displaying the in-vivo image to which the control device 220 has performed the image processing, and a second display device 240 displaying the in-vivo image to which the control device 220 has performed the image processing.

The endoscope 201 includes at least the aforementioned lens unit 501 and imaging unit 502.

The control device 220 includes at least the aforementioned communication module 91, signal processor 92, image processor 93, output selector 94, input unit 95, memory 96, output unit 97, and control unit 98.

The monitor size of the first display device 230 is 31 inches or larger, and preferably 55 inches or larger. Although the monitor size of the first display device 230 is 31 inches or larger, the monitor size is not limited to this, and another monitor size is available. For example, the monitor size has only to enable an image, having a resolution of two mega pixels (for example, a resolution of 1920×1080 pixels, that is, 2K pixels) or more, to be displayed.

The monitor size of the second display device 240 is 31 inches or larger, and preferably 55 inches or larger. Although the monitor size of the second display device 240 is 31 inches or larger, the monitor size is not limited to this, and another monitor size is available. For example, the monitor size has only to enable an image, having a resolution of eight mega pixels (for example, a resolution of 3840×2160 pixels, that is, 4K pixels) or more, and more preferably having a resolution of 32 mega pixels (for example, a resolution of 7680×4320 pixels, that is, 8K pixels) or more, to be displayed. Meanwhile, the second display device 240 has only to be able to display an image having higher resolution than that of the first display device 230. For example, in a case in which the second display device 240 has a monitor size having a resolution of 8K, the first display device 230 may have a monitor size having a resolution of 4K. At this time, the enlargement processor 931 may generate a 4K image, and the resizing processor 933 may generate an 8K image.

According to the second embodiment described above, the flexible endoscope system 200 may also exert a similar effect to that of the aforementioned first embodiment.

Third Embodiment

Next, a third embodiment will be described. Although the endoscope system has been described in the aforementioned first and second embodiments, a case in which the present disclosure is applied to a surgical microscope system will be described in the third embodiment. Note that similar components to those in the endoscope system 1 according to the aforementioned first embodiment are labeled with the same reference signs, and description of the duplicate components is omitted.

Configuration of Surgical Microscope System

Figure 5:
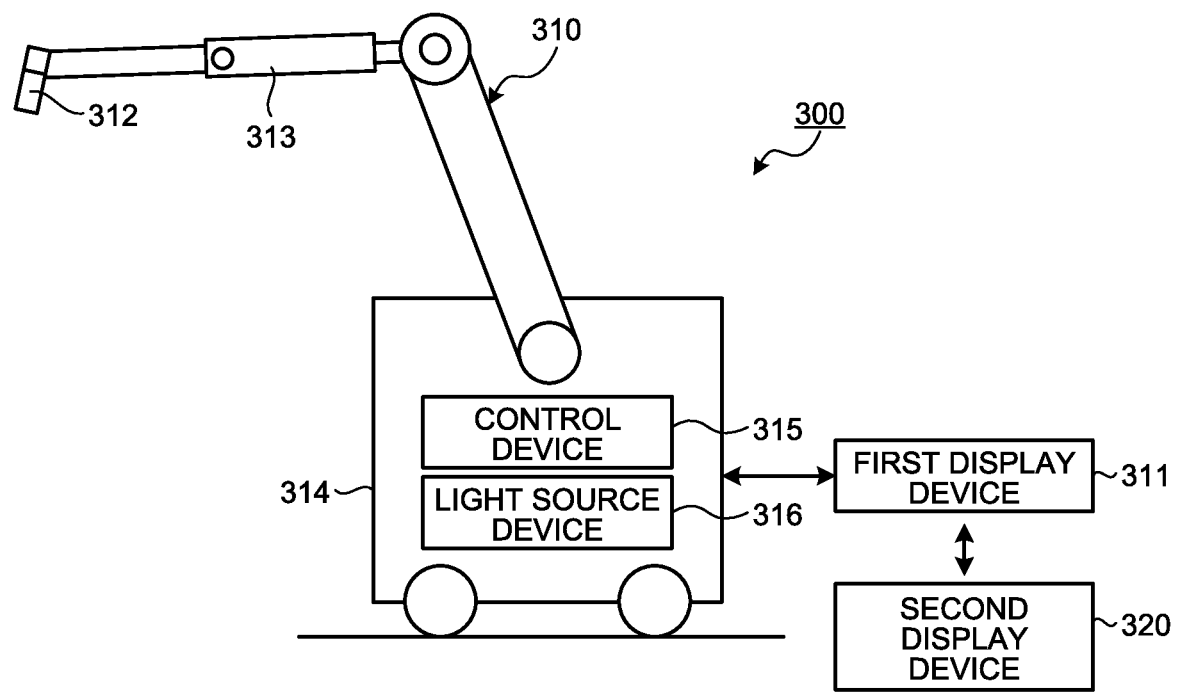
FIG. 5 illustrates a schematic configuration of a surgical microscope system according to a third embodiment.

FIG. 5 illustrates a schematic configuration of a surgical microscope system according to the third embodiment. A surgical microscope system 300 illustrated in FIG. 5 includes a microscope device 310 serving as a medical imaging device capturing and acquiring an image for observation of a subject and a first display device 311 and a second display device 320 displaying the image that the microscope device 310 has captured. Note that the first display device 311 or the second display device 320 and the microscope device 310 may be formed integrally.

The microscope device 310 includes a microscope unit 312 enlarging and capturing a micro part of the subject, a support unit 313 connected to a proximal end of the microscope unit 312 and including an arm turnably supporting the microscope unit 312, and a base unit 314 turnably holding a proximal end of the support unit 313 and movable on a floor surface. The base unit 314 includes a control device 315 controlling operations of the surgical microscope system 300 and a light source device 316 generating illumination light to be emitted from the microscope device 310 to the subject. Meanwhile, the control device 315 includes at least the aforementioned communication module 91, signal processor 92, image processor 93, output selector 94, input unit 95, memory 96, output unit 97, and control unit 98. Also, the base unit 314 may not be provided to be movable on the floor surface but may be secured to a ceiling, a wall surface, or the like to support the support unit 313.

The microscope unit 312 is formed in a cylindrical shape and has therein the aforementioned lens unit 501 and imaging unit 502, for example. The side surface of the microscope unit 312 is provided with a switch receiving input of an instruction for operation of the microscope device 310. An aperture surface of a lower end portion of the microscope unit 312 is provided with cover glass protecting an inside of the microscope unit 312 (not illustrated).

The monitor size of the first display device 311 is 31 inches or larger, and preferably 55 inches or larger. Although the monitor size of the first display device 311 is 31 inches or larger, the monitor size is not limited to this, and another monitor size is available. For example, the monitor size has only to enable an image, having a resolution of two mega pixels (for example, a resolution of 1920×1080 pixels, that is, 2K pixels) or more, to be displayed.

The monitor size of the second display device 320 is 31 inches or larger, and preferably 55 inches or larger. Although the monitor size of the second display device 320 is 31 inches or larger, the monitor size is not limited to this, and another monitor size is available. For example, the monitor size has only to enable an image, having a resolution of eight mega pixels (for example, a resolution of 3840×2160 pixels, that is, 4K pixels) or more, and more preferably having a resolution of 32 mega pixels (for example, a resolution of 7680×4320 pixels, that is, 8K pixels) or more, to be displayed. Meanwhile, the second display device 320 has only to be able to display an image having higher resolution than that of the first display device 311. For example, in a case in which the second display device 320 has a monitor size having a resolution of 8K, the first display device 311 may have a monitor size having a resolution of 4K. At this time, the enlargement processor 931 may generate a 4K image, and the resizing processor 933 may generate an 8K image.

In the surgical microscope system 300 configured as above, a user such as an operator moves the microscope unit 312, performs zooming, and switches illumination light while operating various switches in a state of holding the microscope unit 312. Note that the shape of the microscope unit 312 is preferably a shape causing the microscope unit 312 to extend in an elongated shape in an observation direction so that the user may hold the microscope unit 312 and easily change the viewing direction. For this reason, the shape of the microscope unit 312 may be other than the cylindrical shape and may be a polygonal columnar shape, for example.

According to the third embodiment described above, the surgical microscope system 300 may also exert a similar effect to that of the aforementioned first embodiment.

Other Embodiments

By appropriately combining the plurality of components disclosed in the aforementioned medical observation systems according to the first to third embodiments of the present disclosure, various inventions may be made. For example, some components may be deleted from all of the components described in the aforementioned medical observation systems according to the first to third embodiments of the present disclosure. Also, the components described in the aforementioned medical observation systems according to the first to third embodiments of the present disclosure may appropriately be combined.

Also, in the medical observation systems according to the first to third embodiments of the present disclosure, "unit" described above may be substituted with "means", "circuit", or the like. For example, the control unit may be substituted with the control means or the control circuit.

Also, a program to be executed by the medical observation systems according to the first to third embodiments of the present disclosure is recorded in a computer-readable recording medium such as a CD-ROM, a flexible disk (FD), a CD-R, a digital versatile disk (DVD), a USB medium, and a flash memory as file data in an installable format or in an executable format and is supplied.

Also, the program to be executed by the medical observation systems according to the first to third embodiments of the present disclosure may be configured to be stored on a computer connected to a network such as the Internet, be downloaded via the network, and be supplied.

Meanwhile, in the description of the timing chart in the present specification, although the expressions "first", "then", "subsequently", and the like are used to clarify a processing order of the timings, the processing order to carry out the present disclosure shall not be defined uniquely by these expressions. That is, the processing order in the timing chart described in the present specification may be changed unless it is inconsistent.

Although several embodiments of the present application have been described in detail with reference to the drawings, these embodiments are illustrative only, and the present disclosure may be carried out in another mode, obtained by modifying and improving the embodiments in various ways based on knowledge of those skilled in the art, such as aspects described in the summary of the present disclosure.

The present disclosure exerts an effect of preventing an edge of an image from being blurred and enabling noise to be reduced even in a case in which the image is output to a plurality of display devices having different resolutions.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical image processing device comprising:
   a memory; and
   a processor comprising hardware, wherein the processor is configured to:
     generate, by performing enlargement processing or shrinking processing to first observation image information input from an outside, second observation image information having number of pixels different from predetermined number of pixels, the first observation image information being generated by capturing a subject and having the predetermined number of pixels;
     generate and output third observation mage information by performing enhancement processing for enhancing a structure of the subject to the second observation image information, the structure of the subject being contained in a second observation image corresponding to the second observation image information; and
     generate and output fourth observation image information having different number of pixels from that of the second observation image information by performing enlargement processing or shrinking processing to the third observation image for anon.

2. The medical image processing device according to claim 1, wherein
   the processor is connected to:
     a first circuit to which a first display device that may display an image having an equal number of pixels to that of a third observation image corresponding to the third observation image information is connected; and
     a second circuit to which a second display device that may display an image having an equal number of pixels to that of a fourth observation image corresponding to the fourth observation image information is connected, and the processor is configured to output the third observation image information to the first circuit and output the fourth observation image information to the second circuit.

3. The medical image processing device according to claim 1, wherein the processor is configured to:
perform enlargement processing to the first observation image information to generate the second observation image information; and
perform enlargement processing to the third observation image information to generate the fourth observation image information.

4. The medical image processing device according to claim 3, wherein
the first observation image information has smaller number of pixels than number of pixels of a Full RD image or smaller, and
the processor is configured to:
perform enlargement processing to the first observation image information to generate the second observation image information having the same number of pixels as the Full HD image; and
perform enlargement processing to the third observation image information having the same number of pixels as the Full HD image to generate the fourth observation image information having same number of pixels as a 4K image.

5. The medical image processing device according to claim 1, wherein the processor is configured to:
perform enlargement processing to the first observation image information to generate the second observation image information; and
perform shrinking processing to the third observation image information to generate the fourth observation image information.

6. The medical image processing device according to claim 5, wherein
the first observation image information has smaller number of pixels than number of pixels of a Full HD image or smaller,
the processor is configured to:
perform enlargement processing to the first observation image information to generate the second observation image information having same number of pixels as a 4K image, and
perform shrinking processing to the third observation image information having the same number of pixels as the 4K image to generate the fourth observation image information having the same number of pixels as the Full HD image.

7. The medical image processing device according to claim 1, wherein the processor is configured to:
output the third observation image information to a first display having a first resolution, and
output the fourth observation image information to a second display having a second resolution, different from the first resolution.

8. An image processing method comprising:
generating, by performing enlargement processing or shrinking processing to first observation image information input from an outside, second observation image information having number of pixels different from predetermined number of pixels, the first observation image information being generated by capturing a subject and having the predetermined number of pixels;

generating and outputting third observation image information by performing enhancement processing for enhancing a structure of the subject to the second observation image information, the structure of the subject being contained in second observation image corresponding to the second observation image information; and generating and outputting fourth observation image information having different number of pixels from that of the second observation image information by performing enlargement processing or shrinking processing to the third observation image information.

9. The method according to claim 8, further comprising:
enlargement processing the first observation image information to generate the second observation image information; and
enlargement processing the third observation image information to generate the fourth observation image information.

10. The method according to claim 7, further comprising:
enlargement processing the first observation image information to generate the second observation image information; and
shrinking processing the third observation image information to generate the fourth observation image information.

11. The method according to claim 8, further comprising:
outputting the third observation image information to a first display having a first resolution, and
outputting the fourth observation image information to a second display having a second resolution, different from the first resolution.

12. A non-transitory computer readable recording medium on which an executable program for processing an image, the program instructing a processor to execute:
generating, by performing enlargement processing or shrinking processing to first observation image information input from an outside, second observation image information having number of pixels different from predetermined number of pixels, the first observation image information being generated by capturing a subject and having the predetermined number of pixels;

generating and outputting third observation image information by performing enhancement processing for enhancing a structure of the subject to the second observation image information, the structure of the subject being contained in a second observation image corresponding to the second observation image information; and generating and outputting fourth observation image information having different number of pixels from that of the second observation image information by performing enlargement processing or shrinking processing to the third observation image information.

13. The non-transitory computer readable recording medium according to claim 12, wherein the program further instructs the processor to execute:
enlargement processing to the first observation image information to generate the second observation image information; and
enlargement processing to the third observation image information to generate the fourth observation image information.

14. The non-transitory computer readable recording medium according to claim 12, wherein the program further instructs the processor to execute:

enlargement processing to the first observation image information to generate the second observation image information; and shrinking processing to the third observation image information to generate the fourth observation image information.

15. The non-transitory computer readable recording medium according to claim 12, wherein the program further instructs the processor to execute:

outputting the third observation image information to a first display having a first resolution, and outputting the fourth observation image information to a second display having a second resolution, different from the first resolution.

\* \* \* \* \*